United States Patent [19]

Dockner et al.

[11] Patent Number: 4,824,956

[45] Date of Patent: Apr. 25, 1989

[54] REDUCTIVE DEHALOGENATION OF HALOGEN COMPOUNDS

[75] Inventors: Toni Dockner, Meckenheim; Herbert Krug, Ludwigshafen; Heinz Nohe, Meckenheim, all of Fed. Rep. of Germany

[73] Assignee: BASF Aktiengesellschaft, Ludwigshafen, Fed. Rep. of Germany

[21] Appl. No.: 838,099

[22] Filed: Mar. 10, 1986

[30] Foreign Application Priority Data

Mar. 20, 1985 [DE] Fed. Rep. of Germany ....... 3510033

[51] Int. Cl.⁴ .......................................... C07D 213/48
[52] U.S. Cl. .................................. 546/314; 546/315; 549/70; 549/489; 548/530; 568/437
[58] Field of Search ............... 546/315, 314; 585/641; 549/70, 489; 548/530; 568/437

[56] References Cited

U.S. PATENT DOCUMENTS 3,260,761 7/1966 Burrus et al. ...................... 570/220
4,155,941 5/1979 Nychka et al. ..................... 570/156

FOREIGN PATENT DOCUMENTS 525596 7/1954 Belgium .
1057080 5/1959 Fed. Rep. of Germany .
2216075 12/1983 Japan .

OTHER PUBLICATIONS

Ferrie, J. et al. Chemical Abstracts 102: 166445 y.
Houben–Weyl, Methoden der Organischen Chemie, 4th ed. vol. V/1b, 1972; vol. 5/4, p. 769, 1960.
J. Amer. Chem. Soc. 68 (1946), pp. 261–265.
J. Org. Chem. 29 (1964), pp. 194–198.
J. Org. Chem. 41 (1976) p. 3284.
J. Amer. Chem. Soc. (1968) pp. 1582–1589.
J. Amer. Chem. Soc. (1970) pp. 2849–2856.
J. Org. Chem. 44 (1979) pp. 4774–4781.
Bulletin of the Chemical Society of Japan, vol. 39, 1522–1524 (1966).

*Primary Examiner*—Jane T. Fan
*Attorney, Agent, or Firm*—John H. Shurtleff

[57] ABSTRACT

Aliphatic, cycloaliphatic, aromatic or araliphatic halogen compounds are reductively dehalogenated by reaction with hydrocarbons in the presence of carbon in the liquid phase at from 100° to 450° C. with formation of hydrogen halides.

6 Claims, 1 Drawing Sheet

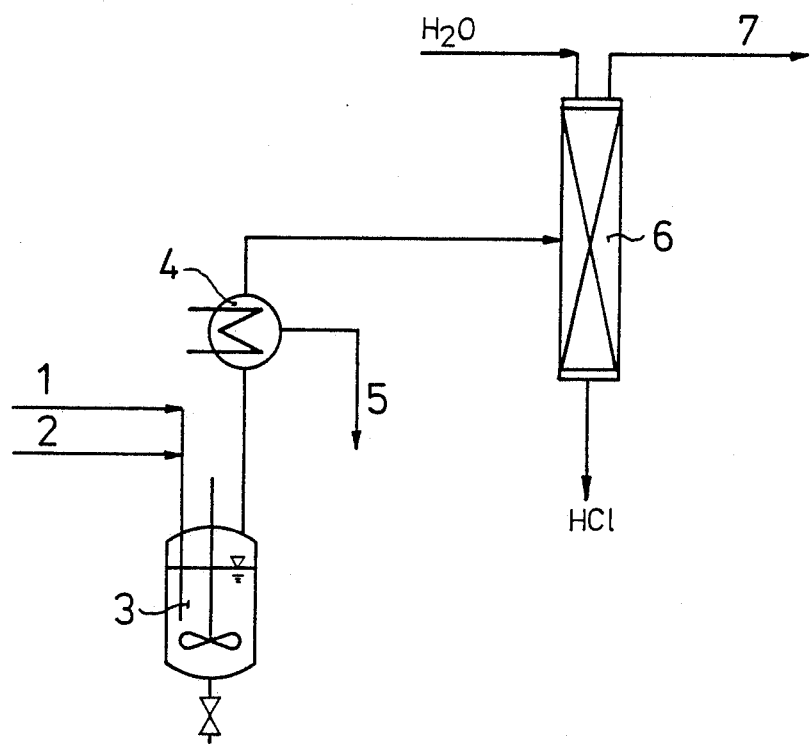

REDUCTIVE DEHALOGENATION OF HALOGEN COMPOUNDS

The invention relates to the reductive dehalogenation of aliphatic, cycloaliphatic, aromatic or araliphatic halogen compounds in which not less than one halogen atom is in a covalent bond with carbon.

It is known to carry out the reductive elimination of vicinal dihalides with metals such as Na, K, Mg, Zn, Cu using organometal compounds or metal hydrides. A summary of these methods can be found in Houben-Weyl, Methoden der Organischen Chemie, 4th edition, Volume V/1b, 1972.

The hydrogenating dehalogenation of aliphatic halogen compounds with Raney nickel in the presence of an amount of alkali equivalent to the halogen has been described in Chem. Ber. 92 (1959), 1700. R. Baltzly and A. P. Phillips (J. Amer. Chem. Soc. 68 (1946), 261-265) describe the catalytic hydrogenolysis of aromatic halogen compounds in neutral or acid aqueous or alcoholic solution using noble metals such as palladium or platinum, for example palladium/animal charcoal or Adams catalyst. According to G. E. Ham and W. P. Coker, olefins which are halogen-substituted in the vinyl or allyl position can be hydrogenated in the presence of rhodium, palladium or platinum to haloalkanes. The yields depend on the solvent, the carrier for the catalyst and the presence of thiophene (J. Org. Chem. 29 (1964), 194-198).

The removal of aromatically bonded halogen and replacement by hydrogen is likewise possible by means of metals such as Na, K or organometallic compounds or even hydrides (see Houben-Weyl, Methoden d. org. Chem., Volume 5/4, page 769, 1960). In addition, halogen can be replaced in the aromatic series by catalytically excited hydrogen. Palladium and Raney nickel are proposed as catalysts.

The selective dehalogenation of acyl chlorides to prepare aldehydes is described in Houben-Weyl, Methoden der organischen Chemie, Volume VII/1, pages 285 et seq. and Volume 4/1c, page 370. In general the method used is the Rosenmund reduction (Merck Index 10th edition ONR-78), whereby acyl chlorides are hydrogenated in the presence of a catalyst such as palladium on barium sulfate. It is frequently necessary to deactivate the catalyst in order to suppress further reduction to the alcohol by adding catalyst poisons, for example "quinoline sulfur" or thiourea. The dehalogenation does not take place when too much sulfur is added or in the presence of phosphorus compounds. It is also crucial for the success of this method that completely dry solvents which need to be free of uncontrollable catalyst poisons are used.

The disadvantage of the reductive dehalogenation methods described is that they have little, if any, feasibility in industry since the reagents are very costly and large amounts of salt, in many cases heavy metal salts, are produced.

Japanese Laid-Open Application No. 216,075/1983 describes a process for dehalogenating polychlorinated biphenyl (PCB), wherein PCB or materials which contain PCB are brought at high temperatures of from 400° to 800° C. into contact with carbon in the gas phase in the absence of oxygen. For example, in this way small amounts (1,000 ppm) of PCB, in solution in hexane, can be vaporized and decomposed over active carbon (5 g).

It is an object of the present invention to provide a process which can be carried out easily in industry, even on a large scale, and is free of the disadvantages described.

We have found that this object is achieved by means of a process for reductively dehalogenating aliphatic, cycloaliphatic, aromatic or araliphatic halogen compounds in which not less than one halogen atom is bonded covalently to carbon, which is advantageously carried out by reacting the halogen compounds with hydrocarbons in the presence of carbon in the liquid phase at from 100° to 450° C. with the formation of hydrogen halides.

The halogen compounds used according to the invention are compounds which carry not less than one halogen atom such as iodine, bromine or chlorine. The aliphatic compounds can be saturated or unsaturated, open-chain or cyclic compounds. It is also possible to cleave araliphatic and aromatic halogen compounds.

The reductive elimination of vicinal dihalides, the cleaving of aromatic halides or the dehalogenation of acyl chlorides is described by equations (a) to (c) below:

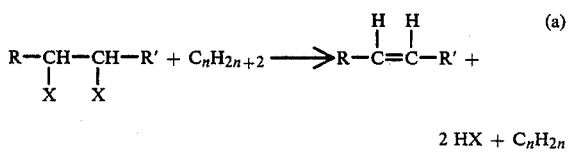

R, R'=H, alkyl, cycloalkyl, aryl, aralkyl
X is Cl, Br, I

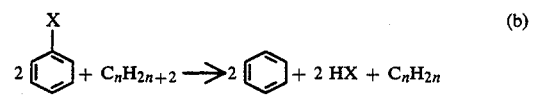

X is Cl, Br, I

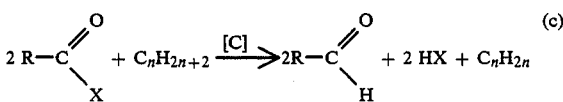

X=halogen
R=aromatic radical

The hydrogen required for the formation of hydrogen halide comes from the hydrocarbon which is converted mainly into carbon, in addition to lower-hydrogen derivatives.

Th hydrocarbons used are advantageously high-boiling mineral oils whose boiling points are higher than the reaction temperature, which is from 100 to 450, preferably from 200 to 400, in particular from 250° to 350° C. Examples of such hydrocarbons are vacuum gas oil, technical white oil, heavy fuel oil, vacum residue oil or other high-boiling constituents obtained in the fractionation of petroleum. It is also possible to use lower-boiling hydrocarbons such as light fuel oil, gasoline, naptha or even liquid gas (cf. Ullmann, Enzyklopädie d. techn. Chemie, 3rd edition, Volume 6, pages 595 to 760, 1955 and 4th edition, Volume 12, pages 570 to 573). In that case, however, elevated pressures are necessary to be able to carry out the reaction in the liquid phase. Crude oils of different provenances can also be used.

The hydrocarbons are advantageously used in an amount of from 10 to 1,000 g, in particular from 20 to 80 g, per mole of halogen compound. To reduce acyl halides, hydrocarbon amounts of from 10 to 2,000 g, in particular from 100 to 1,000 g, per mol of starting material have proved suitable.

Examples of starting materials which are suitable for the reaction according to the invntion are unbranched, branched or cyclic monohaloalkanes such as chloroethane, 1-chloro-2-phenylethane, 1-chloropropane, 1-chloro-2-methylpropane, 2-bromopropane, 1-iodobutane, 1-chloropentane, tert.-butyl iodide, chlorocyclohexane or chlorocyclopentane.

It is also possible to dehalogenate olefinically unsaturated monohalogen compounds, e.g. allyl chloride, 1-bromobut-1-ene, 2-bromobut-2-ene, 1-iodopent-2-ene, 1-chlorocyclohex-1-ene, 1-bromocyclohex-2-ene, cinnamyl chloride or β-bromostyrene, to alkenes.

Particularly suitable starting materials are vicinal dihalides of the general formula I

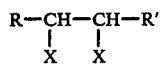

in which X is iodine, bromine and/or chlorine and R and R' are each independently of each other hydrogen, an aliphatic radical, for example alkyl of 1 to 20, in particular 1 to 5, carbon atoms, cycloalkyl, for example of 5 to 8 carbon atoms, aryl or aralkyl, in particular of 6 to 12 carbon atoms, or are, together with the carbon atoms to which they are bonded, a cycloalkane of 4 to 12, in particular 4 to 8, carbon atoms. The process is also advantageous for converting polyhalogen compounds.

Examples of suitable compounds are 1,2-dichloropropane, 1,2-dichlorobutane, 1,2-dichloropentane, 1,2-dibromobutane, 2,3-diiodobutane, 1,2-dibromo-2-methylpropane, 1,2-dibromocyclobutane or 1,2-dibromocyclohexane, 1,2-dichloro-1,2-diphenylethane, 1,2-dichloro-3-phenylpropane, 1-bromo-2-iodobutane, 1-bromo-2-chloroethane and also 1,1,2-trichloroethane and hexachlorocyclohexane (HCH).

The starting compounds described are not meant to limit the range of possible applications for the process according to the invention. The halogen compounds can additionally carry substituents which are inert under the reaction conditions, such as cyano, alkoxy, dialkylamino, phenyl or substituted phenyl groups. It is also possible to convert heterocyclic compounds, for example halogen-substituted pyridine, quinoline, pyrrole or imidazole.

The dehalogenation of hexachlorocyclohexane leads the reaction temperature depending on, to 1,3,5-trichlorobenzene, m-dichlorobenzene, monochlorobenzene and finally benzene.

Examples of aromatic halogen compounds which can be converted are halobenzenes such as bromobenzene, metadichlorobenzene, 1,3,5-trichlorobenzene, halotoluenes such as p-bromotoluene, 2,4-dichlorotoluene, halogenated biphenyls or triphenyls such as diphenyl chloride, triphenyl chloride or polychlorobiphenyl (PCB) and halogenated naphthalenes such as chloronaphthalene, bromonaphthalene, pentachloronaphthalene or hexachloronaphthalene.

The aromatic halogen compounds are substituted by hydrogen. Polyhalogenated aromatics are reductively dehalogenated in stages to the halogen-free hydrocarbon. For instance, the reaction of polychlorobiphenyl with vacuum residue gives hydrogen chloride and diphenyl.

The process according to the invention is very advantageous for the selective reduction of aromatic or hetaromatic acyl halides, in particular bromides or chlorides, to aldehydes. Examples of suitable starting materials are benzoyl chloride, salicyloyl chloride, 1 or 2-naphthoyl chloride, nicotinoyl or isonicotinoyl chloride, picolinoyl chloride, 2-furoyl chloride, thiophene- or pyrrole-2-carbonyl chloride and the corresponding bromides. The radicals mentioned can additionally carry substituents which are inert under the reaction conditions, for example halogen, alkyl, alkoxy, hydroxyl, nitrile, ester, acid or amino groups.

Using the process according to the invention it is also possible to reduce dicarbonyl halides, although in some instances overhydrogenation or cyclization reactions can occur.

The reaction is carried out in liquid phase, in which all or the majority of the reacting hydrocarbons should be present in liquid form. The liquid phase contains suspended carbon which is formed in the course of the reaction; is added; or is present as a constituent of the hydrocarbons. Addition of elemental carbon to the reaction mixture has the effect of speeding up the reaction and increasing the conversion, in particular when the hydrocarbon contains little or no carbon. The reaction mixture preferably contains from 1 to 50, in particular from 5 to 20, % by weight of carbon, based on the hydrocarbon. Examples of suitable carbon additives are petroleum coke and carbon black or some other form of graphite. It is particularly advantageous to use activated carbons such as Carboraffin P ® or animal charcoal, which have been activated for example with $ZnCl_2$, phosphoric acid or hydrogen.

The reaction according to the invention can be carried out batchwise or continuously under atmospheric superatmospheric or reduced pressure in a conventional manner, for example in a stirred reactor or in a cylindrical circulation reactor.

The dehalogenation is advantageously carried out as depicted in the illustration by feeding the halogen compounds (1) in solid, liquid or gas form, with or without an inert gas (2), for example nitrogen, to the reactor (3) together with the hot liquid hydrocarbon phase at reaction temperature. After the reaction, the reaction products leave the reactor in general in gas form together with the resulting hydrogen halide. The products are isolated by condensing them for example, depending on the boiling point, either before or after the hydrogen halide is separated off and if necessary by purifying them, for example by distillation. The hydrogen halide is advantageously separated off by a wash with water. The hydrohalic acids thus obtained are then neutralized or fed to some use. If desired, the hydrogen halide can also be neutralized directly by means of a wash with alkali.

Using the process according to the invention it is surprisingly possible in an inexpensive and technologically simple way to convert potentially polluting toxic halohydrocarbons into less toxic or acceptable compounds. This solves the problem of disposing of these substances which in some instances are used or produced in large amounts in industrial processes without incurring the problems customary with incineration. For the toxicology of halohydrocarbons, in particular chlorohydrocarbons, see Ullmann's Enzyklopädie der techn. Chemie, 4th edition, Volume 9, pages 481 to 490, 521, 522 and 536.

EXAMPLE 1

As can be seen in the depicted apparatus, 40 ml of 1,2-dichloropropane (1) and 8 l of nitrogen (2) were passed per hour at 350° C. through a 2 l stirred flask (3) containing 1.2 kg of the high-boiling mineral oil fraction referred to as vacuum residue.

To be able to maintain the reaction temperature, unconverted dichloropropane was removed from the reaction mixture at 90° C. together with low boilers by condensation (4).

12.75 g of condensate (5) containing 80% by weight of dichloropropane were obtained per hour. This is equivalent to a conversion of 78%. The gaseous reaction products were passed through a wash column (6) to remove the hydrochloric acid. The amount of off-gas (7) produced per hour was 15 l containing 43% by volume of propene. This corresponds to a yield of 90%, based on the conversion. The hourly output of the wash column was 217 g of aqueous HCl containing 10.5% by weight of HCl. This corresponds to 76% of Cl contained in the dichloropropane throughput and corresponds to the conversion.

EXAMPLE 2

Example 1 was repeated, except that 1.2 kg of a paraffinic hydrocarbon fraction referred to as technical white oil was used. 49 g of condensate containing 77% by weight of dichloropropane were obtained per hour, corresponding to a conversion of 17%.

Hydrochloric acid was obtained in an amount of 210 g of 2.43% by weight strength. This corresponds to 17% of the Cl input. 9 l of off-gas containing 8.9% by volume of $C_3H_6$ were obtained. This corresponds to a yield of 51%, based on the conversion.

EXAMPLE 3

Example 1 was repeated, except that 0.75 kg of technical white oil was used together with 0.25 kg of Carboraffin P ®. 14.4 g of condensate containing 64% by weight of dichloropropane were obtained per hour. This corresponds to a conversion of 80%. Also obtained were 225 g of aqueous HCl of 10.5% by weight strength. This corresponds to 79% of the Cl input. 16 l of off-gas containing 41.3% by volume of propene were obtained. This corresponds to a yield of 90%, based on the conversion.

EXAMPLE 4

Example 1 was repeated, except that the hourly input comprised 35 ml of 1,1,2-trichloroethane with 8 l of nitrogen. The hourly output was 14 l of off-gas containing 41.4% by volume of vinyl chloride and 290 g of aqueous hydrochloric acid of 9.31% strength by weight. This corresponds to a conversion of 98% and a yield of 70%, based on the conversion.

EXAMPLE 5

Example 1 was repeated, except that 40 ml of 1,2-dibromobutane together with 4.5 l of nitrogen were used. 14.5 g of condensate containing 76% by weight of dibromobutane were obtained per hour. This corresponds to a conversion of 85%. The output was 385 g of aqueous HBr of 12% by weight strength and 8 l of off-gas containing 40% by volume of but-1-ene. This corresponds to 85% of the starting bromine and a yield of but-1-ene of 50%, based on the conversion.

EXAMPLE 6

Example 1 was repeated, except that the hourly input was 47.5 ml of cyclohexyl chloride together with 4.5 l of nitrogen. Condensation at 0° C. gives 32.6 g of condensate containing 3.7% by weight of cyclohexyl chloride,
73.7% by weight of cyclohexene and
24.2% by weight of cyclohexane.

This corresponds to a conversion of 98%. The yield of cyclohexene is 75% and that of cyclohexane 24%, based on converted cyclohexyl chloride.

EXAMPLE 7

Example 3 was repeated, except that the reaction temperature chosen was 250° C. 49 g of condensate containing 74% by weight of dichloropropane were obtained per hour. This corresponds to a conversion of 21%. 9 l of off-gas containing 10.2% by volume of propene were obtained. This corresponds to a yield of 48%, based on converted dichloropropane.

EXAMPLE 8

Example 1 was repeated, except that 1.2 kg of a high-boiling mineral oil fraction referred to as vacuum gas oil were used. 39 g of condensate containing 85.6% by weight of dichloropropane were obtained per hour. This corresponds to a conversion of 28%. Also obtained were 10.5 l of off-gas containing 22% by volume of propene, which corresponds to a yield of 92%, based on converted dichloropropane.

EXAMPLE 9

The stirred flask (3) (see illustration) was charged with 1.2 g of vacuum residue and 200 g of polychlorinated biphenyl (Clophen), and the temperature was raised to 350° C. 30 hours of gas washing led to the recovery of 122.5 g of HCl, which corresponds to 83.7% of the chlorine contained in the starting Clophen.

Before the gas wash, 205 g of condensate containing 22.7% by weight of dichlorobiphenyl and 8.1% by weight of diphenyl were obtained. From this it can be calculated that 50% of the starting Clophen was hydrogenatingly cleaved to dichlorobiphenyl and 27% to biphenyl.

EXAMPLE 10

The apparatus described in Example 1 was charged with 1 kg of vacuum residue and 73 g of hexachlorocyclohexane, and the temperature was raised. 200° C. saw the start of a pronounced elimination of HCl, which was complete 1 hour later at 250° C. 51 g of condensate obtained before the gas wash contained 63.25% by weight of 1,3-dichlorobenzene
2.47% by weight of 1,2-dichlorobenzene
11.2% by weight of chlorobenzene and
0.25% by weight of benzene.

It can be calculated from these figures that 64% of the starting hexachlorocyclohexane was hydrogenatingly cleaved to 1,3-dichlorobenzene, 14.8% to chlorobenzene, 2.5% to 1,2-dichlorobenzene and 0.5% to benzene.

The gas wash led to the recovery of 428 g of aqueous HCl containing 10.0% by weight of HCl. This corresponds to 57% of the chlorine contained in hexachlorocyclohexane.

EXAMPLE 11

Example 1 was repeated, except that 35 ml of allyl chloride and 8 l of nitrogen were fed per hour. The result obtained per hour was 14 l of off-gas containing 40% by volume of propene and 200 g of aqueous hydrochloric acid of 6.27% by weight strength. This corresponds to a conversion of 80% and a yield of 73%, based on the conversion.

EXAMPLE 12

Example 1 was repeated, except that the hourly input was 17 ml of 1,2-dichlorobenzene with 3 l of nitrogen. The hourly output in terms of condensate was 23.7 g containing 62.4% by weight of 1,2-dichlorobenzene, 21.12% by weight of chlorobenzene and 1.3% by weight of benzene. This corresponds to a conversion of 33%. The yield was 90% of chlorobenzene, based on the conversion. The gas wash produced 107 g of aqueous HCl of 1.7% by weight strength. This corresponds to the resulting chlorobenzene and benzene.

EXAMPLE 13

A 1-l four-necked flask equipped with stirrer, thermometer, inlet tube and distillation attachment was charged with 500 g of technical white oil and 50 g of active carbon powder, and the temperature was raised to 350° C.

40 g of benzoyl chloride were prevaporized at 220° C. from a dropping funnel with 30 l of nitrogen, per hour, and were passed through the inlet tube to underneath the surface of the stirred white oil/carbon mixture. The vapors leaving the reaction flask were cooled down and condensed. The freed hydrogen chloride was absorbed in water. After 3 hours and a total benzoyl chloride feed of 120 g, 130 g of condensate were obtained and found by gas chromatography to contain 18 g of benzoyl chloride and 51 g of benzaldehyde.

For a conversion of 85% this corresponds to a selectivity of 66%.

EXAMPLE 14

The apparatus described in Example 1 was charged with 500 g of technical white oil and 50 g of active carbon powder, and the temperature was raised to 350° C. Per hour 40 g of p-chlorobenzoyl chloride were passed in liquid form with 30 l of nitrogen to underneath the surface of the stirred white oil/carbon mixture. After 3 hours and a total p-chlorobenzoyl chloride feed of 120 g, 125 g of condensate were obtained and found to contain by gas chromatography 24 g of p-chlorobenzoyl chloride and 39 g of p-chlorobenzaldehyde.

For a conversion of 80% this corresponds to a selectivity of 51%.

EXAMPLE 15

The apparatus described in Example 1 was charged with 500 g of technical white oil and 50 g of active carbon powder and heated to 350° C. Per hour 40 g of terephthaloyl dichloride were passed in liquid form with 30 l of nitrogen to underneath the surface of the stirred white oil/carbon mixture. After 3 hours and a total terephthaloyl dichloride feed of 120 g, 115 g of condensate were obtained and found by gas chromatography to contain 25 g of p-tolylaldehyde.

Titration of the resulting hydrochloric acid gave a conversion of 81%. Hence the selectivity was 43%.

EXAMPLE 16

Example 3 was repeated, except that the active carbon was replaced by 50 g of graphite powder. After a period of 3 hours and a total terephthaloyl dichloride feed of 120 g, 128 g of condensate were obtained and found by gas chromatography to contain 34 g of p-tolylaldehyde.

Titration of the resulting hydrochloric acid gave a conversion of 70%. The selectivity was hence 68%.

EXAMPLE 17

The apparatus described in Example 1 was charged with 500 g of technical white oil and 50 g of active carbon powder and heated to 350° C. Per hour 40 g of phthaloyl dichloride were passed in liquid form with 30 l of nitrogen to underneath the surface of the stirred white oil/carbon mixture. After a period of 3 hours and a total phthaloyl dichloride feed of 120 g, 123 g of condensate were obtained and found by gas chromatography to contain 40 g of phthalide.

Titration of the resulting hydrochloric acid gave a conversion of 84%. The selectivity was hence 60%.

EXAMPLE 18

The apparatus described in Example 1 was charged with 500 g of technical white oil and 50 g of active carbon powder and heated to 350° C. Per hour 40 g of nicotinoyl chloride were passed in liquid form together with 27 g of beta-picoline and 30 l of nitrogen to underneath the surface of the stirred white oil/carbon mixture. After a period of 3 hours and a total nicotinoyl chloride feed of 120 g, removal of solid beta-picoline hydrochloride by filtration left 132 g of a liquid discharge which was analyzed by gas chromatography and found to contain 37 g of nicotinaldehyde.

For a 100% conversion this corresponded to a selectivity of 41%.

We claim:

1. A process for preparing an aldehyde by reductively dehalogenating a compound selected from the group consisting of mono- and bicyclic aromatic acyl halides and monocyclic heteroaromatic acyl halide in which the heteroatom is selected from the group consisting of oxygen, nitrogen or sulfur, the aromatic and the heterocyclic rings being unsubstituted or carrying substituents which are inert under the reaction conditions, which process comprises: reacting the acyl halide with a hydrocarbon in the liquid phase in the presence of carbon and at from 100° to 450° C. with the formation of an aldehyde and a hydrogen halide.

2. The process of claim 1, wherein the hydrocarbon used is a high-boiling mineral oil having a boiling point which is higher than the reaction temperature.

3. The process of claim 1 wherein the hydrocarbon is selected from the group consisting of vacuum residue oil, heavy fuel oil and technical white oil.

4. The process of claim 1 wherein the reaction mixture contains from 1 to 50% by weight of carbon, based on the hydrocarbon.

5. The process of claim 1 wherein the hydrocarbon used is a low-boiling hydrocarbon selected from the group of light fuel oil, gasoline, naphtha and liquid gases, and the reaction is carried out under elevated pressure.

6. The process of claim 1 wherein a compound selected from the group consisting of aromatic acyl bromides and chlorides is reacted to form an aldehyde.

* * * * *